(12) United States Patent
Chang et al.

(10) Patent No.: US 9,600,880 B2
(45) Date of Patent: Mar. 21, 2017

(54) METHOD AND SYSTEM FOR QUALIFYING A SURGICAL CLIP APPLIER

(71) Applicant: NATIONAL APPLIED RESEARCH LABORATORIES, Taipei (TW)

(72) Inventors: Han-Chao Chang, Hsinchu (TW); Min-Wei Hung, Hsinchu (TW); Yu-Hsuan Lin, Hsinchu (TW); Cheng-Ru Li, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 23 days.

(21) Appl. No.: 14/880,705

(22) Filed: Oct. 12, 2015

(65) Prior Publication Data

US 2016/0364855 A1    Dec. 15, 2016

(30) Foreign Application Priority Data

Jun. 15, 2015   (TW) .............................. 104119252 A (51) Int. Cl.
```
G06K 9/00      (2006.01)
G06T 7/00      (2006.01)
A61B 17/128    (2006.01)
A61B 17/122    (2006.01)
G02B 21/00     (2006.01)
G02B 21/36     (2006.01)
```

(52) U.S. Cl.
CPC .......... *G06T 7/0012* (2013.01); *A61B 17/122* (2013.01); *A61B 17/1285* (2013.01); *G02B 21/0012* (2013.01); *G02B 21/361* (2013.01); *G02B 21/365* (2013.01); *G06T 2207/10056* (2013.01)

(58) Field of Classification Search
None
See application file for complete search history.

(56) References Cited

U.S. PATENT DOCUMENTS

| | | | | |
|---|---|---|---|---|
| 7,131,977 | B2* | 11/2006 | Fowler | A61B 17/1285 606/138 |
| 2004/0044363 | A1* | 3/2004 | Fowler | A61B 17/1285 606/205 |
| 2007/0021777 | A1* | 1/2007 | Fowler | A61B 17/1285 606/205 |
| 2007/0173866 | A1* | 7/2007 | Sorrentino | A61B 17/122 606/151 |

* cited by examiner

*Primary Examiner* — Nancy Bitar
(74) *Attorney, Agent, or Firm* — Hamre, Schumann, Mueller & Larson, P.C.

(57) ABSTRACT

A method and system for qualifying a surgical clip applier with surgical clips are proposed. After successive firing operations of the surgical clip applier, an image capture unit captures sampling images associated respectively with angularly equidistant radial recesses in a rotatable clip-receiving disk for receiving anything fired from the surgical clip applier. Upon determining that each sampling image contains an individual target image portion showing a single fired surgical clip, a processing unit verifies the qualification of the surgical clip applier based on a predetermined specification and characteristic parameters obtained respectively from the individual target image portions and associated respectively with the surgical clips, which are received respectively in the radial recesses.

11 Claims, 7 Drawing Sheets

METHOD AND SYSTEM FOR QUALIFYING A SURGICAL CLIP APPLIER

CROSS-REFERENCE TO RELATED APPLICATION

This application claims priority to Taiwanese Application No. 104119252, filed on Jun. 15, 2015, the contents of which are hereby incorporated by reference.

FIELD

The disclosure relates to a surgical clip applier, and more particularly to a method and system for qualifying a surgical clip applier.

BACKGROUND

Surgical clip appliers are known in the art and used for a number of distinct and useful surgical procedures. During a laparoscopic surgical procedure, the surgeon often applies a surgical clip using a surgical clip applier to a blood vessel or body tissues so as to prevent the flow of body fluids through the blood vessel or to join the body tissues together. Such surgical clip appliers must be accurately fabricated to ensure their adequate clipping function without causing damage to blood vessels or body tissues during surgical procedures, for example, due to excessive compression of the applied surgical clips. Therefore, it is important for an improved surgical operation to provide a surgical clip applier capable of applying qualified surgical clips.

For inspection of a pack of surgical clip appliers loaded with surgical clips, typically, a predetermined number of the surgical clips, which have been fixed from one surgical clip applier randomly selected from the pack of the surgical clip appliers, are inspected by visually observing, using a microscope, their dimension specifications to determine whether each dimension specification conforms to a predetermined specification. When all the visually observed dimension specifications conform to the predetermined specification, i.e., the surgical clips fired from the selected surgical clip applier are qualified, the pack of the surgical clip appliers passes the inspection accordingly. Otherwise, the pack of the surgical clip applier fails the inspection. In this way, the quality of each surgical clip fired from the selected surgical clip applier may not be ensured due to unintentional human misjudgment. As a result, the inspection result of the pack of the surgical clip applier may be incorrect.

SUMMARY

Therefore, an object of the disclosure is to provide a method and system for qualifying a surgical clip applier that can overcome the aforesaid drawback of the prior art.

According to one aspect of the disclosure, there is provided a method of qualifying a surgical clip applier to be implemented by a system. The surgical clip applier is loaded with a plurality of surgical clips, and has a working tip. The system includes an image capture unit, a rotatable clip-receiving disk disposed adjacent to the working tip of the surgical clip applier, a driving unit for driving the clip-receiving disk to rotate, and a processing unit coupled to the image capture module. The clip-receiving disk has a top surface that is disposed under the image capture unit and that is formed with a plurality of angularly equidistant radial recesses. The method includes the steps of:

a) by the driving unit, driving, in response to a firing operation of the surgical clip applier, the clip-receiving disk to rotate in a manner that one of the radial recesses adjacent to the working tip of the surgical clip applier moves to be aligned with the working tip of the surgical clip applier so as to receive anything ejected from the working tip of the surgical clip applier due to the firing operation of the surgical clip applier;

b) after said one of the radial recesses moves away from the working tip of the surgical clip applier, capturing, by the image capture unit, a sampling image associated with said one of the radial recesses;

c) repeating steps a) and b) until a predetermined number (N) of the sampling images have been captured by the image capture unit, where the predetermined number (N) is not greater than the number of the surgical clips loaded in the surgical clip applier and the number of the radial recesses in the clip-receiving disk;

d) determining, by the processing unit, whether each of the sampling images contains only one individual target image portion showing a single surgical clip ejected from the working tip of the surgical clip applier and received in a respective one of the radial recesses in the clip-receiving disk;

e) upon determining that each of the sampling images contains the individual target image portion, obtaining, by the processing unit, from the individual target image portion of each of the sampling images, a characteristic parameter that is associated with the surgical clip received in the respective one of the radial recesses; and f) verifying, by the processing unit, the qualification of the surgical clip applier based on a predetermined specification and the characteristic parameters, which are obtained respectively from the target image portions of the sampling images.

According to another aspect of the disclosure, there is provided a system for qualifying a surgical clip applier. The surgical clip applier is loaded with a plurality of surgical clips, and has a working tip. The system includes:

a support frame used to hold and position the surgical clip applier;

a rotatable clip-receiving disk disposed under and adjacent to the working tip of the surgical clip applier, the clip-receiving disk, having a top surface that is formed with a plurality of angularly equidistant radial recesses;

a driving unit configured to drive, in response to each of a number (N+1) of successive firing operations of the surgical clip applier, the clip-receiving disk to rotate in a manner that one of the radial recesses adjacent to the working tip of the surgical clip applier moves to be aligned with the working tip or the surgical clip applier so as to receive anything ejected from the working tip of the surgical clip applier due to the firing operation of the surgical clip applier, the number (N) being not greater than the number of the surgical clips loaded in the surgical clip applier and the number of the radial recesses in the clip-receiving disk;

an image capture unit connected electrically to the driving unit, mounted to the support frame and disposed above the top surface of the clip-receiving disk, the image capture unit being controlled by the driving unit to capture, in response to each of second to $(N+1)^{th}$ ones of the successive firing operations of the surgical clip applier, a sampling image associated with a corresponding one of the radial recesses that has been previously aligned with and is currently adjacent to the working tip of the surgical clip applier so as to obtain a number (N) of the sampling images associated respectively with the corresponding ones of the radial recesses; and a processing unit connected electrically to the linage capture unit for receiving the sampling images therefrom, the processing unit being configured to determine whether each of the sampling images contains only one individual target image portion showing a single surgical clip ejected from the working tip of the surgical clip applier and received in a respective one of the radial recesses in the clip-receiving disk, upon determining that each of the sampling images contains the individual target image portion, obtain, based on the individual target image portion of each of the sampling images, a characteristic parameter that is associated with the surgical clip received in the respective one of the radial recesses, and verify the qualification of the surgical clip applier based on a predetermined specification and the characteristic parameters, which are obtained respectively from the individual target image portions of the sampling images.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
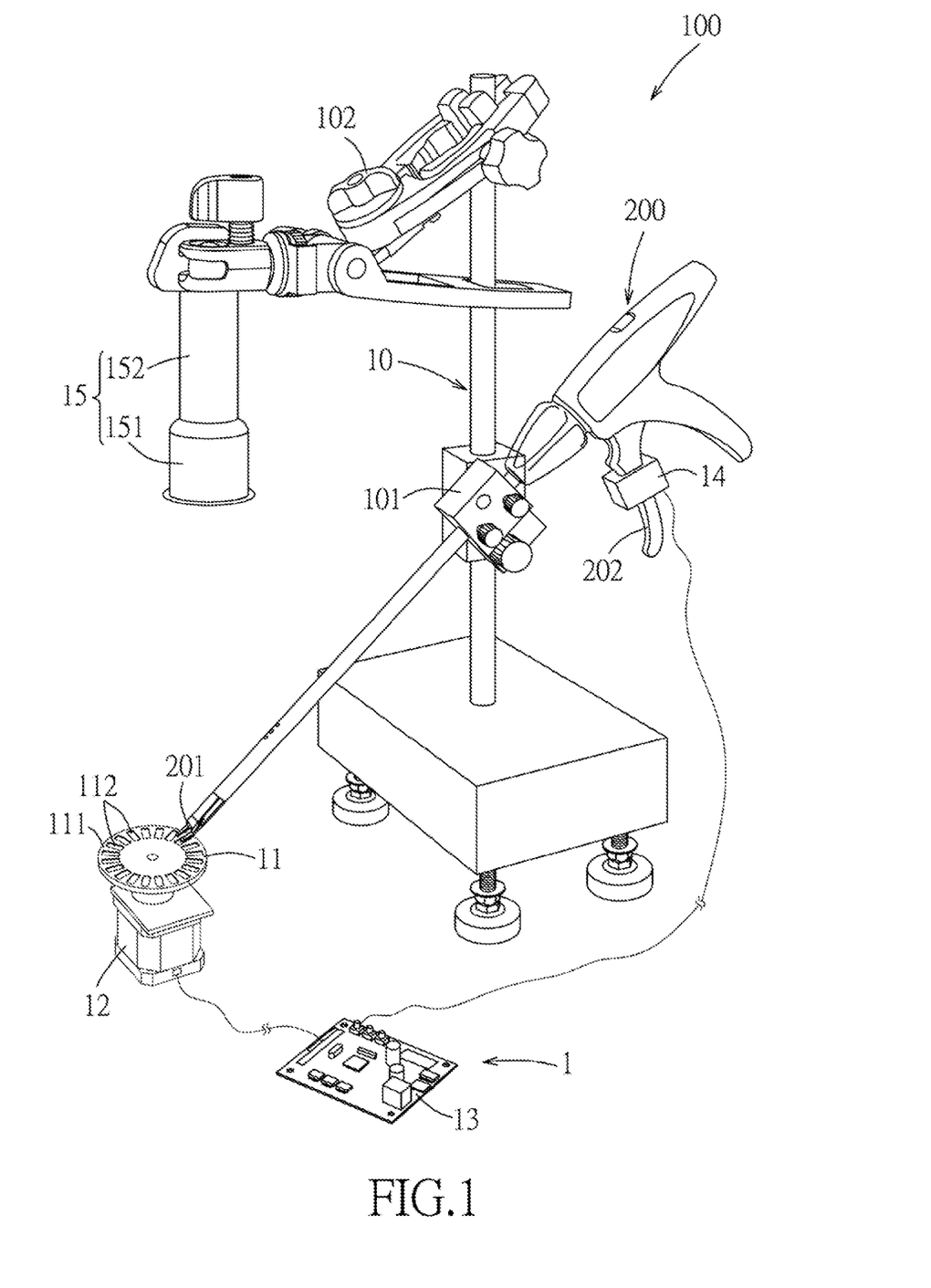
FIG. 1 is a schematic view showing the embodiment of a system for qualifying a surgical clip applier according to the disclosure.
Figure 2:
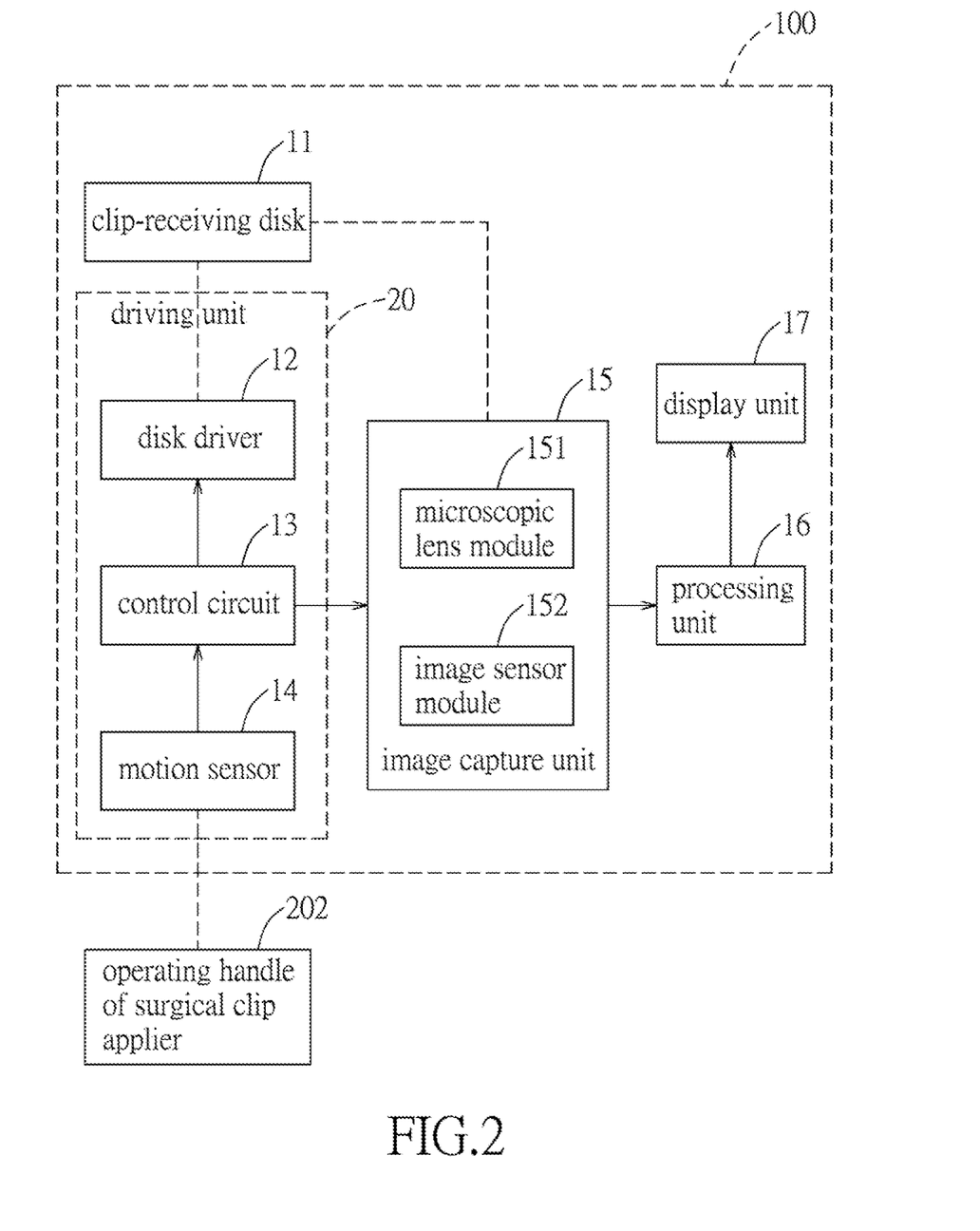
FIG. 2 is a schematic block diagram illustrating operative relationships among components of the system of the embodiment.
Figure 3:
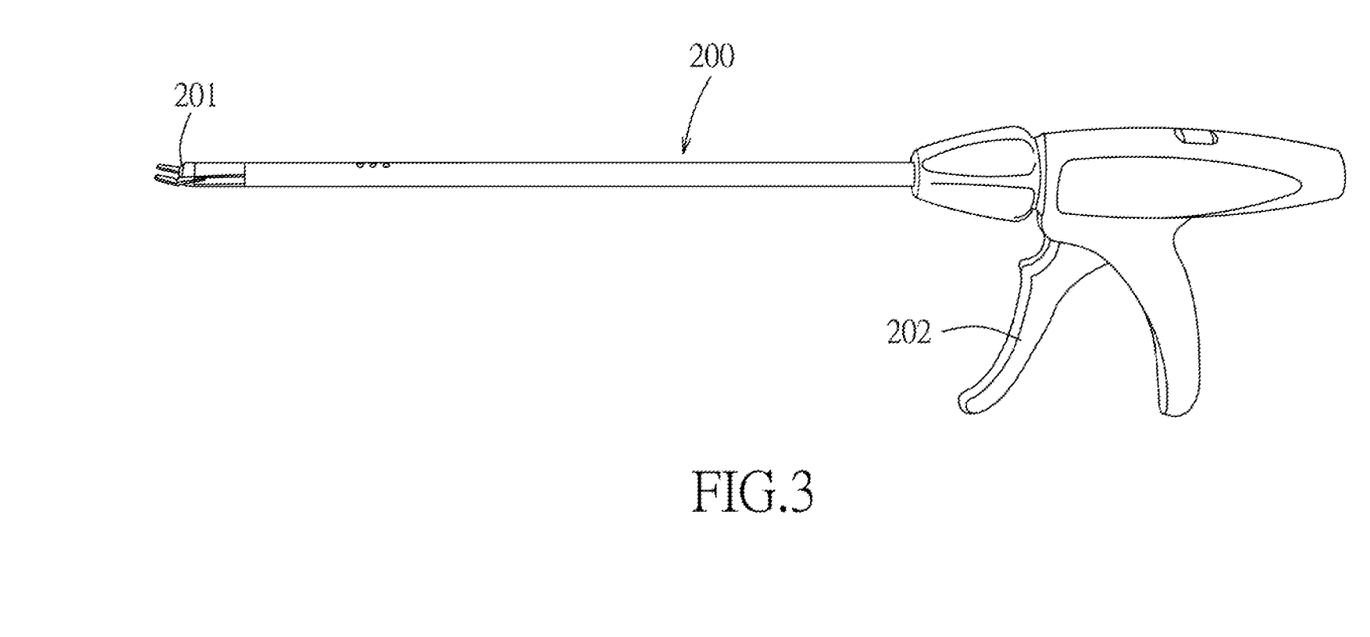
FIG. 3 is a schematic view of an example of the surgical clip applier.

Referring to FIGS. 1 to 3, the embodiment of a system 100 for qualifying a surgical clip applier 200 according to this disclosure is shown to include a support frame 10, a rotatable clip-receiving disk 11, a driving unit 20, an image capture unit 15, a processing unit 16 and a display unit 17.

In this embodiment, the surgical clip applier 200 is loaded with a plurality of surgical clips (not shown in the drawing), and includes a working tip 201 and a rotatable operating trigger 102. In use, the surgical clip applier 200 normally ejects a single surgical clip out of the working tip 201 after each firing operation actuated by pressing the operating trigger 202. Since the feature of this disclosure does not reside in the configuration of the surgical clip applier 200, which is known to those skilled in the art, details of the same are omitted herein for the sake of brevity.

Figure 4:
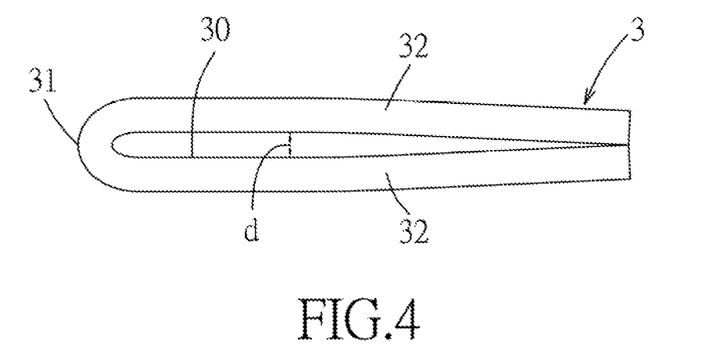
FIG. 4 exemplarily illustrates a surgical clip fired from the surgical clip applier.

FIG. 4 exemplarily illustrates a surgical clip 3 ejected from the working tip 201 of the surgical clip applier 200. The surgical clip 3 is U-shaped and includes an arched base 31 and two opposite clamp arms 32. A clamping area 30 defined among the arched base 31 and the clamp arms 32 is used to receive a body tissue or blood vessel to be clipped.

As shown in FIG. 1, the support frame 10 includes an adjustable first holding module 101 used to hold and position the surgical clip applier 200, and an adjustable second holding module 102 disposed above the first holding module 101.

Figure 5:
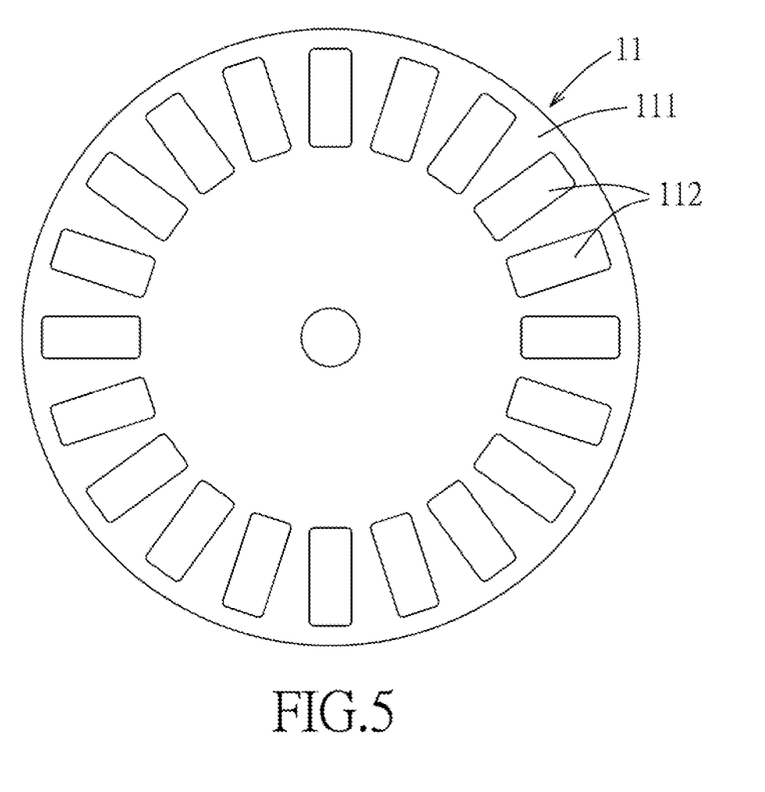
FIG. 5 is a schematic top view showing a rotatable clip-receiving disk of the system of the embodiment.

Referring to FIGS. 1, 2 and 5, the clip-receiving disk 11 is disposed under and adjacent to the working tip 201 of the surgical clip applier 200. The clip-receiving disk 11 has a top surface 111 that is formed with a plurality of angularly equidistant radial recesses 112.

The image capture unit 15 is mounted to the support frame 10, is held and positioned by the second holding module 102 of the support frame 10, and is disposed above the top surface 111 of the clip-receiving disk 11. The image capture unit 15 is connected electrically to and controlled by the driving unit 20.

The driving unit 20 is configured to drive, in response to each of a number (N+1) of successive firing operations of the surgical clip applier 200, the clip-receiving disk 11 to rotate in a manner that one of the radial recesses 112 moves to be aligned with the working tip 201 of the surgical clip applier 200 to as to receive anything ejected from the working tip 201 of the surgical clip applier 200 due to the firing operation of the surgical clip applier 200.

Figure 6:
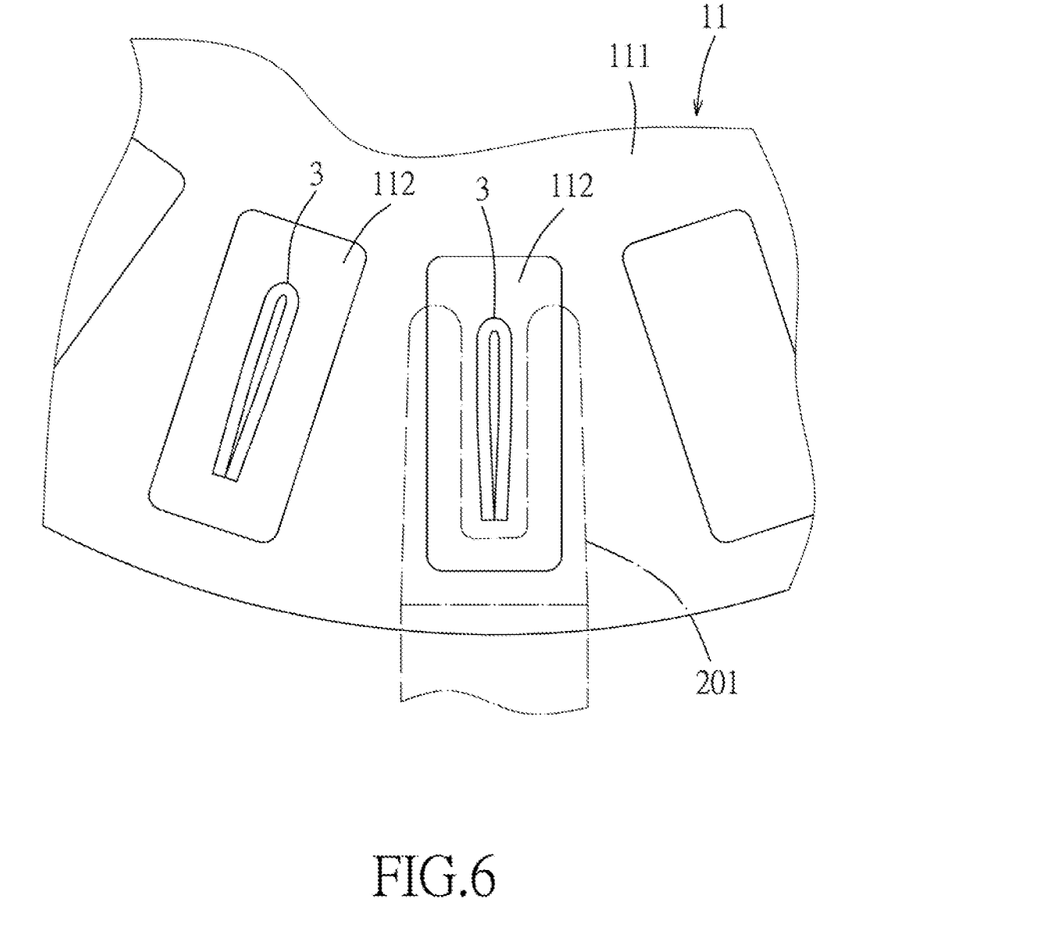
FIG. 6 is a fragmentary schematic top view exemplarily illustrating the clip-receiving disk in a state of use.

FIG. 6 exemplarily illustrates two surgical clips 3 ejected from the working tip 201 in response to two successive firing operations of the surgical clip applier 200 and received respectively in two adjacent ones of the radial recesses 112. It is noted that the number (N) is not greater than the number of the surgical clips loaded in the surgical clip applier 200 and the number of the radial recesses 112. In this embodiment, for example, the number N is 20, and the number of the radial recesses 112 is 20.

Referring to FIGS. 1 and 2, the driving unit 20 includes a motion sensor 14, a disk driver 12 and a control circuit 13.

The motion sensor 14 is adapted to be attached to the operating trigger 202 of the surgical clip applier 200 for sensing motion of the operating trigger 202 to generate a trigger signal upon detecting motion of the operating trigger 202 for actuating one firing operation.

The disk driver 12, such as a motor, is disposed under the clip-receiving disk 11, and includes a rotatable drive shaft (not shown in the drawings) connected to the clip-receiving disk 11. Thus, the clip-receiving disk 11 is rotatable with the drive shaft.

The control circuit 13 is connected electrically to the motion sensor 14, the disk driver 12 and the image capture unit 15. The control circuit 13 controls the disk driver 12 to drive the clip-receiving disk 11 to rotate in the above manner in response to receipt of the trigger signal, which corresponds to each of the number (N+1) of the successive firing operations of the surgical clip applier 200, from the motion sensor 14. On the other hand, the control circuit 13 further controls the image capture unit 15 to capture a sampling image associated with a corresponding one of the radial recesses 112 that has been previously aligned with and is adjacent to the working tip 201 of the surgical clip applier 200 in response to receipt of the trigger signal from the motion sensor 14.

Figure 8:
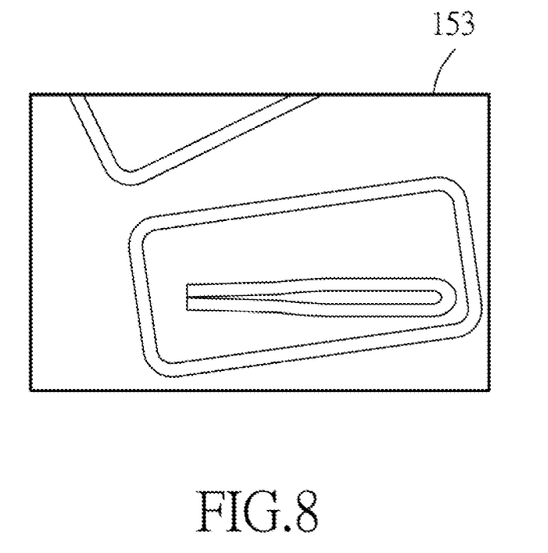
FIG. 8 exemplarily illustrates a sampling image captured by an image capture unit of the embodiment.

In this embodiment, the image capture unit 15 includes a microscopic lens module 151 and an image sensor module 152. The microscopic lens module 151 is configured to collect light of an image of a corresponding one of the radial recesses 112 and magnify the image of the corresponding one of the radial recesses in response to each of the second to $(N+1)^{th}$ ones of the successive firing operations of the surgical clip applier 200. The image sensor module 152 is mechanically coupled to the microscopic lens module 151, and is configured to sense the light collected by the microscopic lens module 151 to generate the sampling image that corresponds to the magnified image of the corresponding one of the radial recesses 112 in response to each of the second to $(N+1)^{th}$ of the continuous firing operations of the surgical clip applier 200. FIG. 8 exemplarily illustrates one sampling image 153 captured by the image capture unit 15.

Figure 7:
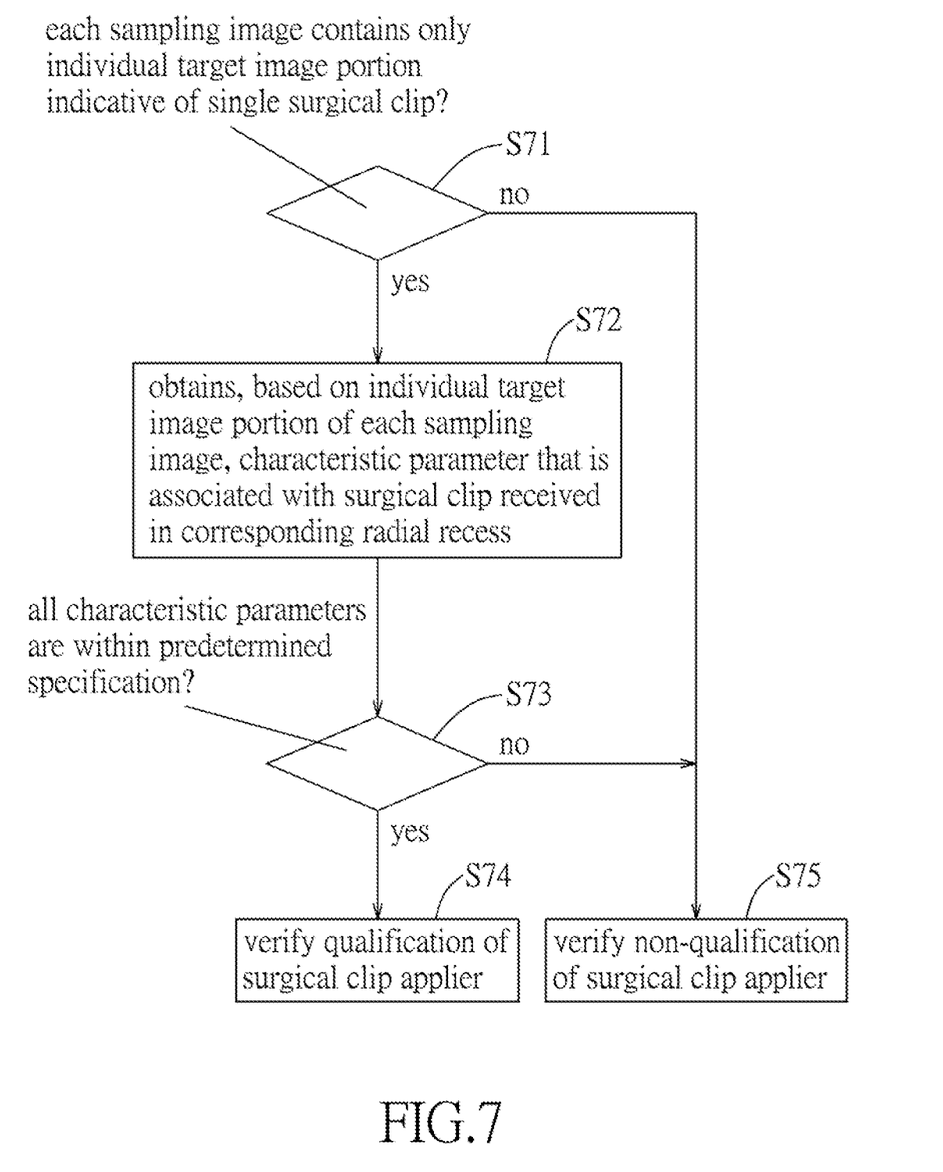
FIG. 7 is a flow chart illustrating how a processing unit of the embodiment qualifies the surgical clip applier.

Referring again to FIG. 2, the processing unit 16 is connected electrically to the image capture unit 15 for receiving the number (N) of the sampling images therefrom. FIG. 7 is a flow chart illustrating how the processing unit 16 qualifies the surgical clip applier 200 based on the sampling images from the image capture unit 15.

In step S71, the processing unit 16 determines, using image recognition technology, whether each of the sampling images contains only one individual target image: portion showing a single surgical clip ejected from the working tip 201 of the surgical clip applier 200 and received in a corresponding one of the radial recesses 112 in the clip-receiving disk 11. If the result of the determination is affirmative, the flow proceeds to step S72. If the processing unit 16 determines that any one of the sampling images contains none of a target image portion showing a single ejected surgical clip or has an image portion showing two or more ejected surgical clips, the processing unit 16 verifies non-qualification of the surgical clip applier 200 (step S75). For example, if a dry firing operation of the surgical clip applier 200 occurs in any one of the first to $N^{th}$ ones of the successive firing operations, the sampling image corresponding to this dry firing operation should not have a target image portion showing a single ejected surgical clip. On the other hand, if two or more surgical clips are abnormally fired in any one of the first to $N^{th}$ ones of the successive firing operations and are received together in the same radial recess 112, a corresponding sampling image may contain an image portion showing two or more ejected surgical clips.

Figure 9:
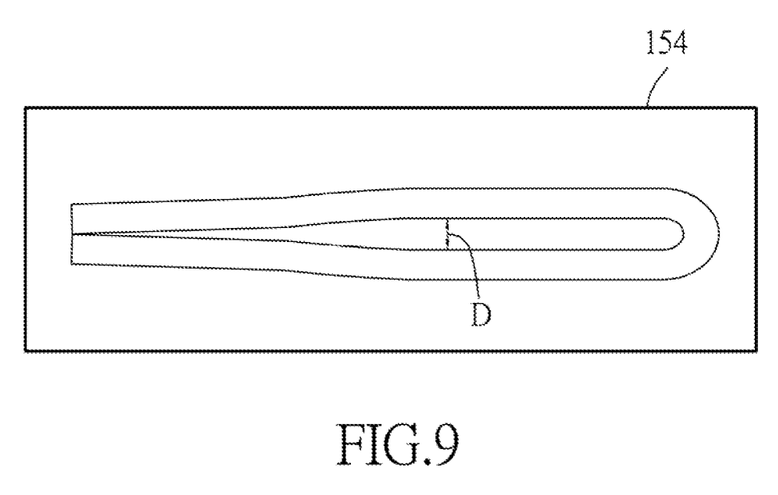
FIG. 9 exemplarily illustrates a target image portion contained in the sampling image of FIG. 8.

In step S72, when the processing unit 16 determines that each sampling image contains the individual target image portion, the processing unit 16 obtains, using image recognition technology, from the individual target image portion of each sampling image, a characteristic parameter that is associated with the rejected surgical clip received in the respective one of the radial recesses 112. For example, the characteristic parameter is the largest gap between the clamp arms of the ejected surgical clip received in the respective one of the radial recesses 112. FIG. 9 exemplarily illustrates an individual target image portion 154 contained in the sampling image 153 of FIG. 8. In this embodiment, referring again to FIG. 4, for each surgical clip 3 ejected from the working tip 201 of the surgical clip applier 200, a largest gap (d) between the clamp arms 32 is defined as its characteristic parameter. The processing unit 16 calculates the physical largest gap (d) of the surgical clip 3 based on a largest distance (D) between the clamp arms in the individual target image portion 154 of the sampling image, as shown in FIG. 9.

In step S73, the processing unit 16 determines whether all the largest gaps (i.e., the characteristic parameters) obtained respectively from the individual target image portions of the sampling images are within a predetermined gap range that is regarded as a predetermined specification in this embodiment. For example, for a 4.5 mm-type surgical clip, the predetermined gap range is from about 0.002 inches to about 0.0025 inches. In other words, the processing unit 16 verifies qualification of each ejected surgical clip by determining whether the characteristic parameter of each ejected surgical clip conforms to the predetermined specification in step S73. If the result of the determination is affirmative, the flow proceeds to step S74. In this case, the qualification of each surgical clip fired from the surgical clip applier 200 is successfully verified by the processing unit 16. Otherwise, the flow goes to step S75.

In step S74, when the processing unit 16 determines that all the largest gaps are within the predetermined gap range, the processing unit 16 verifies the qualification of the surgical clip applier 200.

In this embodiment, the processing unit 16 further generates a verification result that is associated with qualification or non-qualification of each of the surgical clips fired from the surgical clip applier 200 and the qualification or non-qualification of the surgical clip applier 200. The display unit 17 is connected electrically to and controlled by the processing unit 16 for displaying the verification result. It is noted that, for example, the processing unit 16 and the display unit 17 may be embodied in a computer device, such as a notebook computer or a personal computer.

In such a configuration, the driving unit 20 can automatically control rotation of the clip-receiving disk 11 and operation of the image capture unit 15 in response to successive firing operations of the surgical clip applier 200. In addition, the processing unit 16 can accurately verify the qualification of the surgical clip applier 200 and each surgical clip fired from the surgical clip applier 200 using image recognition technology. Furthermore, the verification result associated with the surgical clip applier 200 and the surgical clips fired from the surgical clip applier 200 is displayed on the display unit 17 for convenience of an inspector, and may be utilized for further statistics and/or analysis. Therefore, for a mass of the surgical clip appliers, the system 100 of this disclosure can easily and accurately qualify the surgical clip appliers, and can prevent the aforesaid incorrect inspection due to unintentional human misjudgment in the prior art.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method of qualifying a surgical clip applier to be implemented by a system, the surgical clip applier being loaded with a plurality of surgical clips and having a working tip, the system including an image capture unit, a rotatable clip-receiving disk, a driving unit and a processing unit, the clip-receiving disk being disposed under the image capture unit and formed with a plurality of angularly equidistant radial recesses, said method comprising the steps of:
   a) by the driving unit, driving, in response to a firing operation of the surgical clip applier, the clip-receiving disk to rotate in a manner that one of the radial recesses adjacent to the working tip of the surgical clip applier moves to be aligned with the working tip of the surgical clip applier so as to receive anything ejected from the working tip of the surgical clip applier due to the firing operation of the surgical clip applier;

b) after said one of the radial recesses moves away from the working tip of the surgical clip applier, capturing, by the image capture unit, a sampling image associated with said one of the radial recesses;

c) repeating steps a) and b) until a number (N) of the sampling images have been captured by the image capture unit, where the number (N) is not greater than the number of the surgical clips loaded in the surgical clip applier and the number of the radial recesses in the clip-receiving disk;

e) determining, by the processing unit, whether each of the sampling images contains only one individual target image portion snowing a single surgical clip ejected from the working tip of the surgical clip applier and received in a respective one of the radial recesses in the clip-receiving disk;

e) upon determining that each of the sampling images contains the individual target image portion, obtaining, by the processing unit, from the individual target image portion of each of the sampling images, a characteristic parameter that is associated with the surgical clip received in the respective one of the radial recesses; and f) verifying, by the processing unit, the qualification of the surgical clip applier based on a predetermined specification and the characteristic parameters, which are obtained respectively from the target image portions of the sampling images.

2. The method as claimed in claim 1, the image capture unit including a microscopic lens module, and an image sensor module mechanically coupled to the microscopic lens module, wherein step b) includes the sub-steps of:

b1) after said one of the radial recesses moves away from the working tip of the surgical clip applier, by the microscopic lens module, collecting light of an image of said one of the radial recesses to the image capture module, and magnifying the image of said one of the radial recesses; and b2) sensing, by the image sensor module, the light collected by the microscopic lens module to generate the sampling image that corresponds to the magnified image of said one of the radial recesses.

3. The method as claimed in claim 1, each of the surgical clips ejected from the working tip of the surgical clip applier being U-shaped and including an arched base, and opposite clamp arms connected to the arched base, wherein:

in step e), for each of the surgical clips, which are received respectively in the corresponding ones of the radial recesses, a largest gap between the clamp arms is defined as its characteristic parameter; and in step f), the predetermined specification includes a predetermined gap range.

4. The method as claimed in claim 3, wherein step f) includes the sub-steps of:

f1) determining, by the processing unit, whether all the largest gaps obtained respectively from the individual target image portions of the sampling images are within the predetermined gap range; and f2) upon determining that all the largest gaps obtained respectively from the individual target image portions of the sampling images are within the predetermined gap range, verifying, by the processing unit, the qualification of the surgical clip applier.

5. The method as claimed in claim 3, wherein, in step f), the predetermined gap range is from about 0.002 inches to about 0.0025 inches.

6. A system for qualifying a surgical clip applier, the surgical clip applier being loaded with a plurality of surgical clips and having a working tip, said system comprising a support frame used to hold and position the surgical clip applier;

a rotatable clip-receiving disk disposed under and adjacent to the working tip of the surgical clip applier, said clip-receiving disk having a top surface that is formed with a plurality of angularly equidistant radial recesses;

a driving unit configured to drive, in response to each of a number (N+1) of continuous firing operations of the surgical clip applier, said clip-receiving disk to rotate in a manner that one of said radial recesses adjacent to the working tip of the surgical clip applier moves to be aligned with the working tip of the surgical clip applier so as to receive anything ejected from the working tip of the surgical clip applier due to the firing operation of the surgical clip applier, the number (N) being not greater than the number of the surgical clips loaded in the surgical clip applier and the number of said radial recesses in said clip-receiving disk;

an image capture unit connected electrically to said driving unit, mounted to said support frame and disposed above said top surface of said clip-receiving disk, said image capture unit being controlled by said driving unit to capture, in response to each of second to $(N+1)^{th}$ ones of the successive firing operations of the surgical clip applier, a sampling image associated with a corresponding one of said radial recesses that has been previously aligned with and is currently adjacent to the working tip of the surgical clip applier so as to obtain a number (N) of the sampling images associated respectively with the corresponding ones of said radial recesses; and a processing unit connected electrically to said image capture unit for receiving the sampling images therefrom, said processing unit being configured to determine whether each of the sampling images contains only an individual target image portion indicative of a single surgical clip ejected from the working tip of the surgical clip applier and received in a respective one of said radial recesses in said clip-receiving disk, upon determining that each of the sampling images contains the individual target image portion, obtain, based on the individual target image portion of each of the sampling images, a characteristic parameter that is associated with the surgical clip received in the respective one of the racial recesses, and verify the qualification of the surgical clip applier based on a predetermined specification and the characteristic parameters, which are obtained respectively from the target image portions of the sampling images.

7. The system as claimed in claim 6, each firing operation of the surgical clip applier being actuated through rotation of an operating- trigger of the surgical clip applier, wherein said driving unit includes:

a motion sensor configured to be attached to the operating trigger for sensing motion of the operating trigger of the surgical clip applier to generate a trigger signal upon detecting motion of the operating trigger for actuating one firing operation;

a disk driver including a rotatable drive shaft connected to said clip-receiving disk; and a control circuit connected electrically to said motion sensor, said disk driver and said image capture unit, said control circuit controlling said disk driver to drive said clip-receiving disk to rotate in the manner in response to receipt of the trigger signal from said motion sensor that corresponds to each of the number (N+1) of the successive firing operations of the surgical clip applier, and controlling said image capture unit to capture the sampling image associated with the respective one of said radial recesses in response to receipt of the trigger signal, which corresponds to each of the second to $(N+1)^{th}$ ones of the successive firing operations of the surgical clip applier, from said motion sensor.

8. The system as claimed in claim 6, wherein said image capture unit includes:

a microscopic lens module disposed adjacent to said clip-receiving disk, and configured to collect light of an image of a corresponding one of said radial recesses, and to magnify the image of the corresponding one of said radial recesses in response to each of the second to $(N+1)^{th}$ ones of the successive firing operations of the surgical clip applier; and an image sensor module mechanically coupled to said microscopic lens module, and configured to sense the light collected by said microscopic lens module to generate the sampling image that corresponds to the magnified image of the corresponding one of said radial recesses in response to each of the second to $(N+1)^{th}$ ones of the successive firing operations of the surgical clip applier.

9. The system as claimed in claim 6, each of the surgical clips ejected from the working tip of the surgical clip applier being U-shaped and including bed base, and opposite clamp arms connected to the arched base, wherein:

for each of the surgical clips, which are received respectively in the respective ones of said radial recesses, a largest gap between the clamp arms is defined as its characteristic parameter; and the predetermined specification includes a predetermined gap range.

10. The system as claimed in claim 9, wherein said processing unit is configured to determine whether all the largest gaps obtained respectively from the individual target image portions of the sampling images are within the predetermined gap range; and verify the qualification of the surgical clip applier upon determining that all the largest gaps obtained respectively from the individual target image portions of the sampling images are within the predetermined gap range.

11. The system as claimed in claim 9, wherein the predetermined gap range is from about 0.002 inches to about 0.0025 inches.

* * * * *